(12) United States Patent
Cassell

(10) Patent No.: US 7,638,159 B2
(45) Date of Patent: Dec. 29, 2009

(54) LIQUID MASKING FOR SELECTIVE COATING OF A STENT

(75) Inventor: Robert Cassell, Otsego, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 208 days.

(21) Appl. No.: 11/839,665

(22) Filed: Aug. 16, 2007

(65) Prior Publication Data

US 2008/0065202 A1    Mar. 13, 2008

Related U.S. Application Data

(60) Provisional application No. 60/843,859, filed on Sep. 12, 2006.

(51) Int. Cl.
*A61L 33/00* (2006.01)
(52) U.S. Cl. .............. 427/2.24; 427/2.3; 427/2.25; 427/2.28; 424/426; 428/41.7; 428/41.8; 428/352; 428/354
(58) Field of Classification Search ............. 424/426; 427/2.3, 2.24; 428/41.7
See application file for complete search history.

(56) References Cited

U.S. PATENT DOCUMENTS

| 3,438,809 A | 4/1969 | Kaveggia et al. |
| 5,092,877 A | 3/1992 | Pinchuk |
| 5,304,121 A | 4/1994 | Sahatjian |
| 5,464,650 A * | 11/1995 | Berg et al. ............ 427/2.3 |
| 5,509,899 A | 4/1996 | Fan et al. |
| 5,612,107 A * | 3/1997 | Sangani et al. ......... 428/41.7 |
| 5,693,034 A | 12/1997 | Buscemi et al. |
| 5,755,770 A | 5/1998 | Ravenscroft |
| 5,788,979 A * | 8/1998 | Alt et al. ............... 424/426 |
| 5,824,046 A | 10/1998 | Smith et al. |
| 5,879,697 A | 3/1999 | Ding et al. |
| 6,099,562 A | 8/2000 | Ding et al. |
| 6,120,847 A | 9/2000 | Yang et al. |
| 6,221,646 B1 | 4/2001 | Dwarki et al. |
| 6,258,121 B1 | 7/2001 | Yang et al. |
| 6,358,556 B1 | 3/2002 | Ding et al. |
| 6,569,195 B2 | 5/2003 | Yang et al. |
| 6,645,547 B1 | 11/2003 | Shekalim et al. |
| 6,766,817 B2 | 7/2004 | da Silva |
| 6,776,793 B2 | 8/2004 | Brown et al. |
| 6,885,770 B2 | 4/2005 | Matsuura |
| 6,916,379 B2 | 7/2005 | Shekalim et al. |

(Continued)

FOREIGN PATENT DOCUMENTS

WO    WO 00/32238 A1 *    6/2000

(Continued)

OTHER PUBLICATIONS

U.S. Appl. No. 60/843,859, filed Sep. 12, 2006, Cassell.

*Primary Examiner*—Michael Barr
*Assistant Examiner*—Andrew Bowman
(74) *Attorney, Agent, or Firm*—Vidas, Arrett & Steinkraus, P.A.

(57) ABSTRACT

The present invention relates to a method for masking the inner surface of a tubular medical device with a fluid in order to selectively coat the outer surface of the tubular medical device. The inner lumen of the tubular medical device is filled with the fluid prior to deposition of a coating to the outer surface.

22 Claims, 13 Drawing Sheets

U.S. PATENT DOCUMENTS

| | | |
|---|---|---|
| 6,918,404 B2 | 7/2005 | Dias da Silva |
| 7,048,962 B2 | 5/2006 | Shekalim et al. |
| 7,066,586 B2 | 6/2006 | da Silva |
| 2004/0073290 A1 | 4/2004 | Chouinard |
| 2004/0213893 A1 | 10/2004 | Boulais |
| 2004/0215169 A1 | 10/2004 | Li |
| 2005/0069630 A1 | 3/2005 | Fox et al. |
| 2005/0182480 A1 | 8/2005 | Doran et al. |

FOREIGN PATENT DOCUMENTS

| | | | |
|---|---|---|---|
| WO | 2005025455 | | 3/2005 |
| WO | WO 2006/055799 | * | 5/2006 |
| WO | 2007133348 | | 11/2007 |

* cited by examiner

LIQUID MASKING FOR SELECTIVE COATING OF A STENT

CROSS-REFERENCE TO RELATED APPLICATIONS

This Application claims priority from U.S. Provisional Patent Application No. 60/843,859, filed on Sep. 12, 2006, the entire content of which is herein incorporated by reference.

FIELD OF THE INVENTION

The present invention relates to the field of insertable and/or implantable medical devices, in particular, stents.

BACKGROUND OF THE INVENTION

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to prevent restenosis following angioplasty in the vascular system. They may be self-expanding, expanded by an internal radial force, such as when mounted on a balloon, or a combination of self-expanding and balloon expandable (hybrid expandable).

A stent is typically an open tubular structure that has a pattern (or patterns) of apertures extending from the outer surface of the stent to the lumen. It is common to make stents of biocompatible metallic materials, with the patterns cut on the surface with a laser machine. The stent can be electropolished to minimize surface irregularities since these irregularities can trigger or stimulate foreign body reactions or adverse biological responses such as thrombosis or restenosis.

Another way to further minimize such responses is by coating insertable and/or implantable medical devices with a variety of coating compositions including those comprising a biocompatible polymer. These coatings may also further incorporate therapeutic agents or biologically active materials. For example, implanted stents have been used to carry therapeutic agents such as thrombolytic agents.

See, for example, commonly assigned U.S. Pat. Nos. 6,885,770, 6,569,195, 6,358,556, 6,258,121, 6,120,847, 6,099,562, and 5,304,121 and U.S. Pat. Nos. 5,879,697 and 5,092,877, each of which is incorporated by reference herein in its entirety. See also commonly assigned 2004/0215169 which is incorporated by reference herein in its entirety.

Such coatings have been applied to the surface of a medical device by various methods, such as spray coating and dip coating. It can be difficult, when employing such conventional methods, for example, to coat only the outer surface without coating the inner surface of a tubular stent wall which has openings therein. Also, the ratio of coating thickness placed on the inner surface of the tubular wall and placed on the outer surface of the tubular wall created by a conventional method is fixed and cannot be varied. For example, when a dip coating method is employed, the thickness of the coating varies depending upon the geometry of the stent since the coating tends to collect where struts intersect and difficult to vary using such a method.

Furthermore, in some medical devices having a tubular wall, all of the surfaces of the medical device or portions thereof may not require coating, or may not require a coating which includes a biologically active material. For instance, the inner surface of a stent may not need a coating containing a biologically active material when the biologically active material is intended to be delivered to a body lumen wall, which only directly contacts the outer surface of the stent. The inner surface of the stent does not come in direct contact with the body lumen wall and does not apply the biologically active material to the body lumen wall. On the other hand, if the biologically active material is intended to be delivered to a body fluid rather than a body lumen wall, then the coating containing the biologically active material should be placed on the inner surface of the stent wall but is not needed on the outer surface.

In addition, it may be advantageous to apply different coatings on different portions of the tubular wall. For example, an expandable stent is often crimped into a reduced diameter state for delivery through a body lumen to the site of stent deployment. Therefore, it is advantageous that the coating on portions of the stent which contact each other in the stent's crimped state do not stick to one another which can result in damage to the coating. If the stent is balloon expandable and therefore crimped onto an expandable balloon member, the inner surface of the stent that contacts the balloon should not stick to the balloon during withdrawal of the balloon after the stent has been deployed. A lubricious outer surface facilitates smooth delivery through a body lumen.

There remains a need in the art for a method of coating a medical device comprising a tubular wall, such as a stent, which provides the ability to control placement of the coating on selected stent surfaces, such as the outer surface, but not the inner surface of the tubular wall.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention relates to an improved method of selectively coating an insertable and/or implantable medical device having a tubular wall, the tubular wall having an inner surface and an outer surface, the inner surface of the tubular wall defining a central lumen, and wherein the method allows for selectively coating the outer surface of the tubular wall only.

In one aspect, the present invention relates to a method of selectively coating the outer surface of the tubular wall by filling the central lumen defined by the inner surface of the tubular wall with a fluid, allowing the outer surface to dry or actively drying the outer surface of the tubular wall, and then coating the outer surface of the tubular wall with the desired coating.

The central lumen of the tubular medical device can be filled by submersing the medical device in any suitable fluid having a surface tension such that the fluid is retained within the central lumen defined by the inner surface of the tubular wall of the medical device.

Both polar and non-polar solvents can be used herein. Suitable solvents may be selected based on the surface tension characteristics of the solvent.

The outer surface of the tubular wall may be selectively coated with any suitable stent coating which may include therapeutic agents, lubricious materials, biocompatible polymers, etc. These materials are mixed into a suitable solvent or co-solvent blend. The mixture can be applied to the outer surface using any suitable coating method such as by spraying, brushing, roll coating, etc. without disturbing the masking fluid filling the central lumen.

Once the desirable coating is applied to the outer surface and allowed to dry, the fluid retained in the central lumen of the tubular structure may then be removed using any suitable technique.

The present invention is particularly suitable for coating insertable and/or implantable medical devices having a small inner diameter, defined by the inner surface of the tubular wall of the medical device. One example of such a device is a stent employed in cardiovascular applications.

These and other aspects, embodiments and advantages of the present invention will become immediately apparent to those of ordinary skill in the art upon review of the Detailed Description and Claims to follow.

BRIEF DESCRIPTION OF THE DRAWINGS

FIGS. 4a-1 and 4b-1 are optical digital views of a stent with its central lumen filled with masking fluid, in this embodiment, toluene, and FIGS. 4a-2 and 4b-2 are simplified line art diagrams of the optical digital views showing placement of reference characters and leadlines.

DETAILED DESCRIPTION OF THE INVENTION

Figure 1:
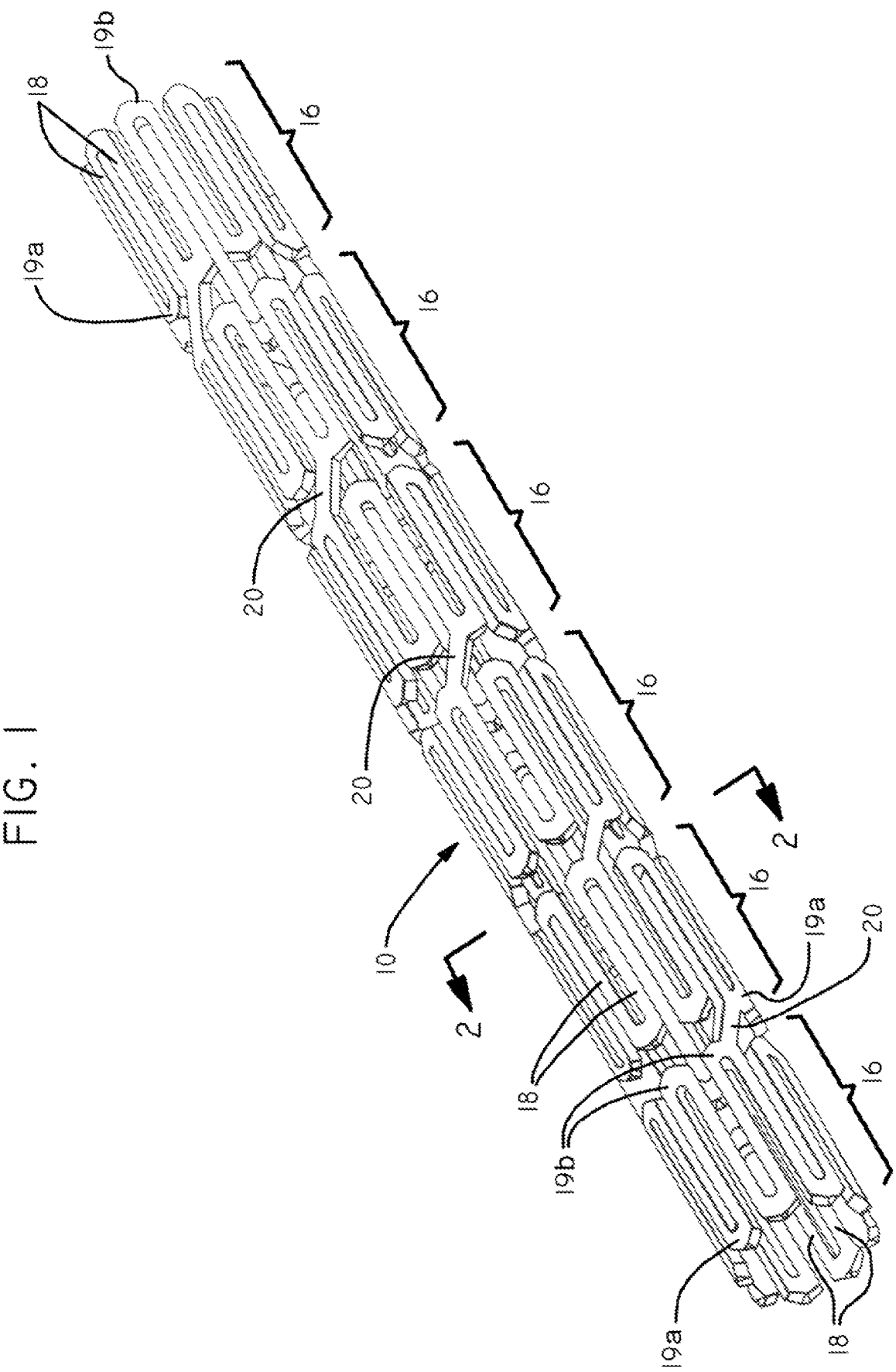
FIG. 1 shows a perspective view of one embodiment of a stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

In its broadest aspect, the present invention relates to a method of using a liquid to mask the inner surface of a medical device having a tubular wall, the tubular wall having an inner surface and an outer surface and openings which extend from the outer surface to the inner surface, the inner surface defining a central lumen, wherein the liquid mask allows selective coating of the outer surface. The surface tension of the liquid results in retention of the liquid in the inner lumen of the tubular medical device which is defined by the inner surface of the tubular wall.

The present invention finds particular utility for selectively coating the outer surface of a tubular stent. Turning now to the figures, FIG. 1 is a perspective view of one embodiment of a stent 10 prior to application of any coating, show in an unexpanded state. Stents are well known structures. Stents of the type shown in FIG. 1 are disclosed in commonly assigned copending U.S. Pat. No. 6,776,793, the entire content of which is incorporated by reference herein. FIG. 1 is shown for illustrative purposes only, and not as a limitation on the scope of the present invention. Any stent design can be employed with the coating method according to the invention. Other stent designs are found in commonly assigned copending Patent Application Publication Nos. 20040073290 and 20050182480, each of which is incorporated by reference herein in its entirety. Such examples are intended for illustrative purposes only and are not intended to limit the scope of the present invention.

The stent configuration shown in FIG. 1 can be seen to be made up of a plurality of adjacent segments or undulating bands generally indicated at 16, each of which is formed in an undulating flexible pattern of substantially parallel struts 18. Pairs of struts are interconnected at alternating end portions 19a and 19b. The end portions as shown are generally elliptical but may be rounded or square or pointed or the like. Any configuration of end portions is acceptable.

Interconnecting elements 20 extend from one end portion 19b of one segment 16 to another end portion 19a of another adjacent segment 16. While in the embodiment shown in FIG. 1 there are at least three interconnecting elements joining adjacent first and second bands, fewer or additional interconnecting elements are also contemplated. The number of interconnecting elements 20 may vary depending on circumstances in any particular instance.

Figure 2:
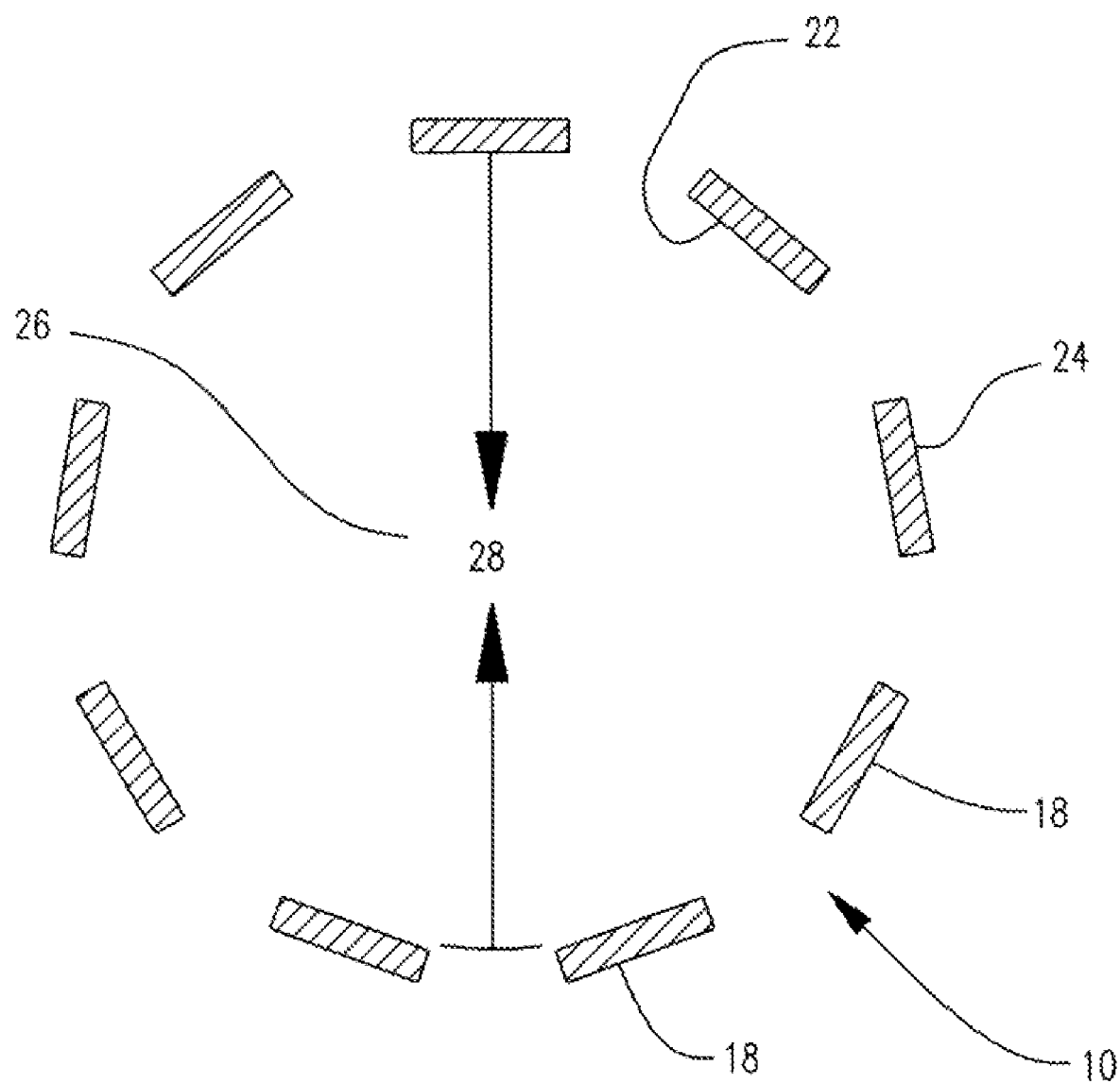
FIG. 2 is a radial cross-section taken at section 2-2 in FIG. 1.

FIG. 2 is a radial cross-section taken at section 2-2 in FIG. 1. As can be seen from FIG. 2, stent 10 has an inner surface 22 and an outer surface 24. Inner surface 22 defines the central lumen 26 of stent 10 and has a diameter 28.

The stents according to the invention, may suitably be formed from any suitable biocompatible stent material, including metals and metal alloys such as stainless steel, cobalt alloys such as cobalt-chromium alloys such as eligiloy, tantalum or other plastically deformable metals, titanium alloys such as nickel-titanium alloys (shape memory alloy) commonly referred to as Nitinol, other titanium alloys, platinum tungsten alloys, etc. Polymers and ceramics may also be employed. Stent materials are commonly selected based on mechanical properties, corrosion resistance and vascular compatibility.

The invention also contemplates the use of more than one material in the formation of the stents. For example, the first undulating bands and the second undulating bands may be made of different materials. Optionally, the connectors may be made of a different material than the first and/or second undulating bands.

The inventive stents may be provided in mechanically expandable form, in self-expanding form or as a hybrid of the two. Mechanically expandable stents, in accordance with the invention, may be expanded using any suitable mechanical device including a balloon.

The stents may be formed using any suitable method as is known in the art. For example, patterns may be cut in a thin walled tube using any suitable method. A preferred method is to cut patterns in the tube with a laser. However, chemical etching or EDM (electrical discharge machining), stamping a flat sheet, or molding the stent with the desired design are also contemplated. Furthermore, the sheet can be extruded, or the sheet may also be rolled and welded prior to forming the desired pattern therein. Stents may also be formed from one or more interwoven wires or braids.

Once the pattern has been formed in the stent, the stent can be electro-polished to minimize surface irregularities, and then cleaned using any suitable method known in the art. The stent is then ready for application of a coating or coatings.

Figure 3:
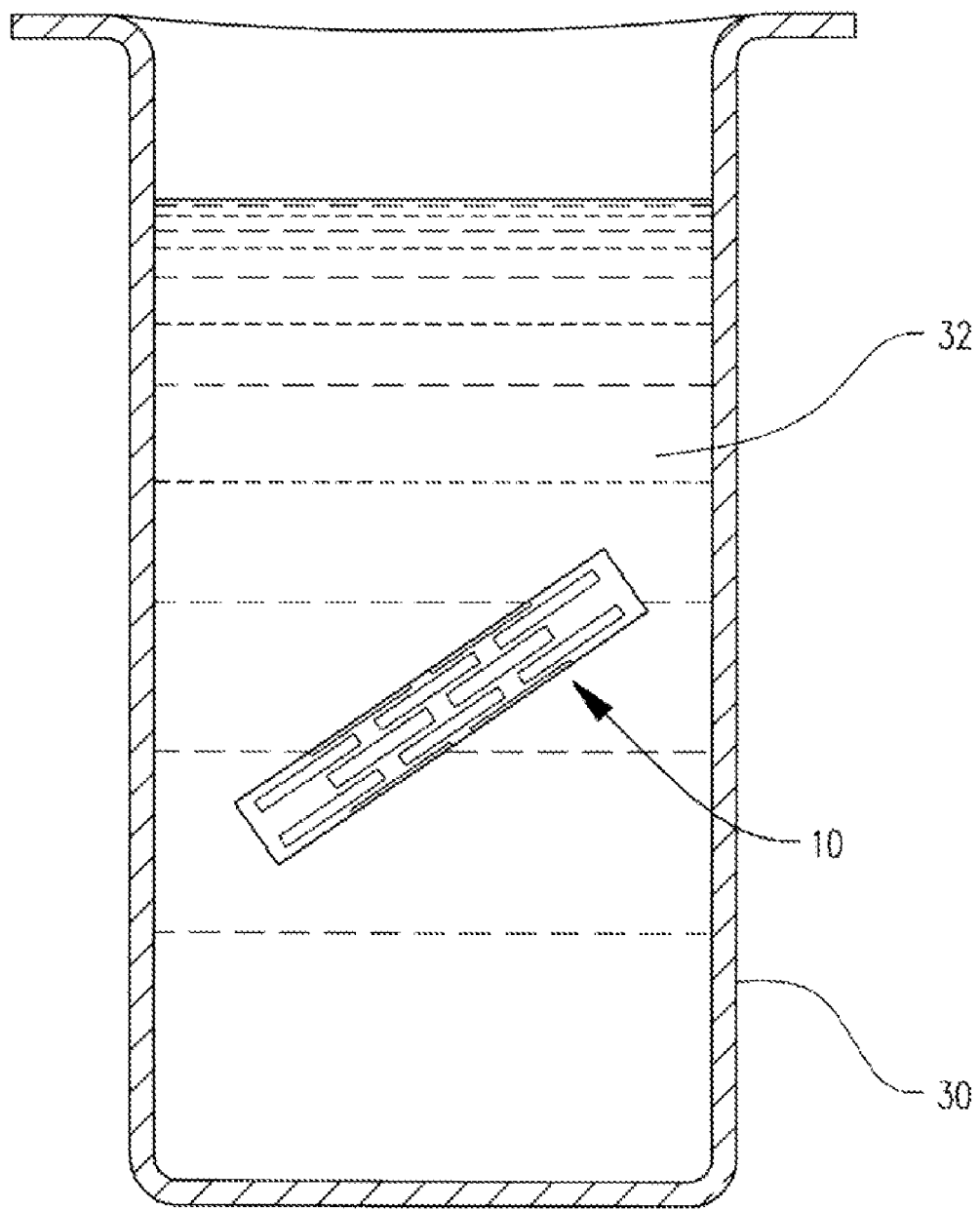
FIG. 3 is a side view of a stent submersed in a vessel of masking fluid.

In a first coating step according to the invention, the central lumen 26 of the tubular stent 10 is filled with the masking fluid. This may be accomplished using any suitable method. One way to achieve this is to submerse stent 10 in a vessel 30 of the desired masking fluid 32, such as water or hydrocarbon solvent, as shown generally in FIG. 3. Any suitable masking fluid may be employed providing that it has a surface tension sufficient to be retained within the stent.

Once the stent 10 has been fully submersed in the masking fluid 32, it is then removed from the masking fluid 32. Upon removal of the stent from the masking fluid, it is desirable that the masking fluid 32 fill the central lumen 28 of the stent 10 and remain there during coating of the outer surface of the tubular stent wall.

It has been found that the surface tension of some fluids result in the fluid filling the central lumen and the voids in the stent wall and the fluid is retained therein by the surface tension of the fluid. Relatively higher surface tension fluids, i.e., those with strong molecular attraction to one another, can result in better fluid retention within the central lumen. The fluid can stick to the inside filaments of the stent structure and can span the small interstitial spaces, i.e. openings in the tubular wall of the stent. Other masking fluid parameters include viscosity, surface energy as it relates to the interaction between the masking fluid and the stent surface, rate of evaporation and fluid density.

The size of the central lumen of the stent also contributes to the ability to retain fluid therein. For example, for some stents employed in the coronary arteries, inner diameters may be in the range of about 1 to about 4 mm. While small diameter sizes are a factor in the stents ability to retain the fluid within the lumen, the surface tension as a function of the internal volume to surface area ratio also plays a role.

The length of these stents may be in the range of about 8 mm to about 32 mm and the internal volume ($\pi r^2 \times$length) is therefore in the range of about 6 mm$^3$ to about 400 mm$^3$. The surface area of these stents (circumference×length=$2\pi r \times$length) is about 25 mm$^2$ to about 400 mm$^2$.

There are other factors which also contribute to the ability to retain fluid within the central lumen, however, including for example, stent design and the distance between stent struts, surface energy of the stent material, which all contribute to the capillary forces which hold the masking fluid in place.

Suitable fluids include both polar and non-polar solvents. Polarity is a relative scale with water being at the high end of the scale, and some hydrocarbon solvents such as cyclohexane being at the other end of the scale.

Examples of suitable polar solvents exhibiting relatively high surface tension include, but are not limited to, water and glycerol which have high surface tensions.

Other suitable polar solvents include, but are not limited to, ethylene glycol, benzyl alcohol, dimethyl sulfoxide (DMSO), t-butyl acetate, ethyl acetate, tetrahydrofuran, acetone, methyl ethyl ketone, acetonitrile, N,N-dimethylformamide, etc.

Examples of suitable non-polar solvents include, but are not limited to, hydrocarbon solvents such as toluene and xylene, for example, and carbon tetrachloride.

While the solvents have been classified herein according to polarity, the invention is independent of the polarity of the solvent, and the solvent may be selected more based on its surface tension characteristics.

Furthermore, as noted above, it is also the inner diameter 28 of the stent 10 as shown in FIG. 2, in addition to the surface tension of the fluid employed, also which contributes to the ability of the stent 10 to retain the masking fluid 32 within the central lumen 26 once the stent 10 has been removed from the masking fluid 32.

Figures 1, 4A:
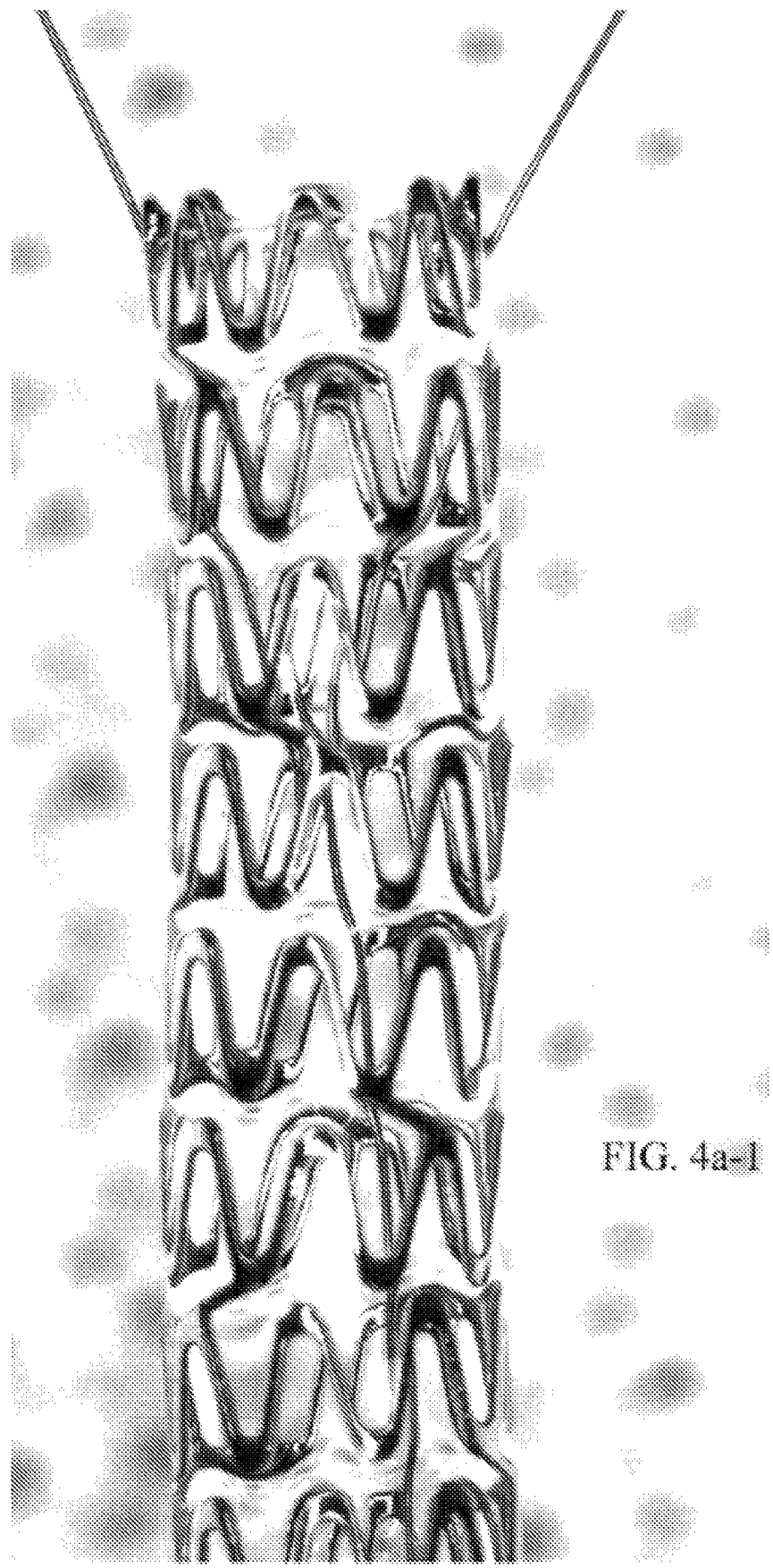
Figures 2, 4A:
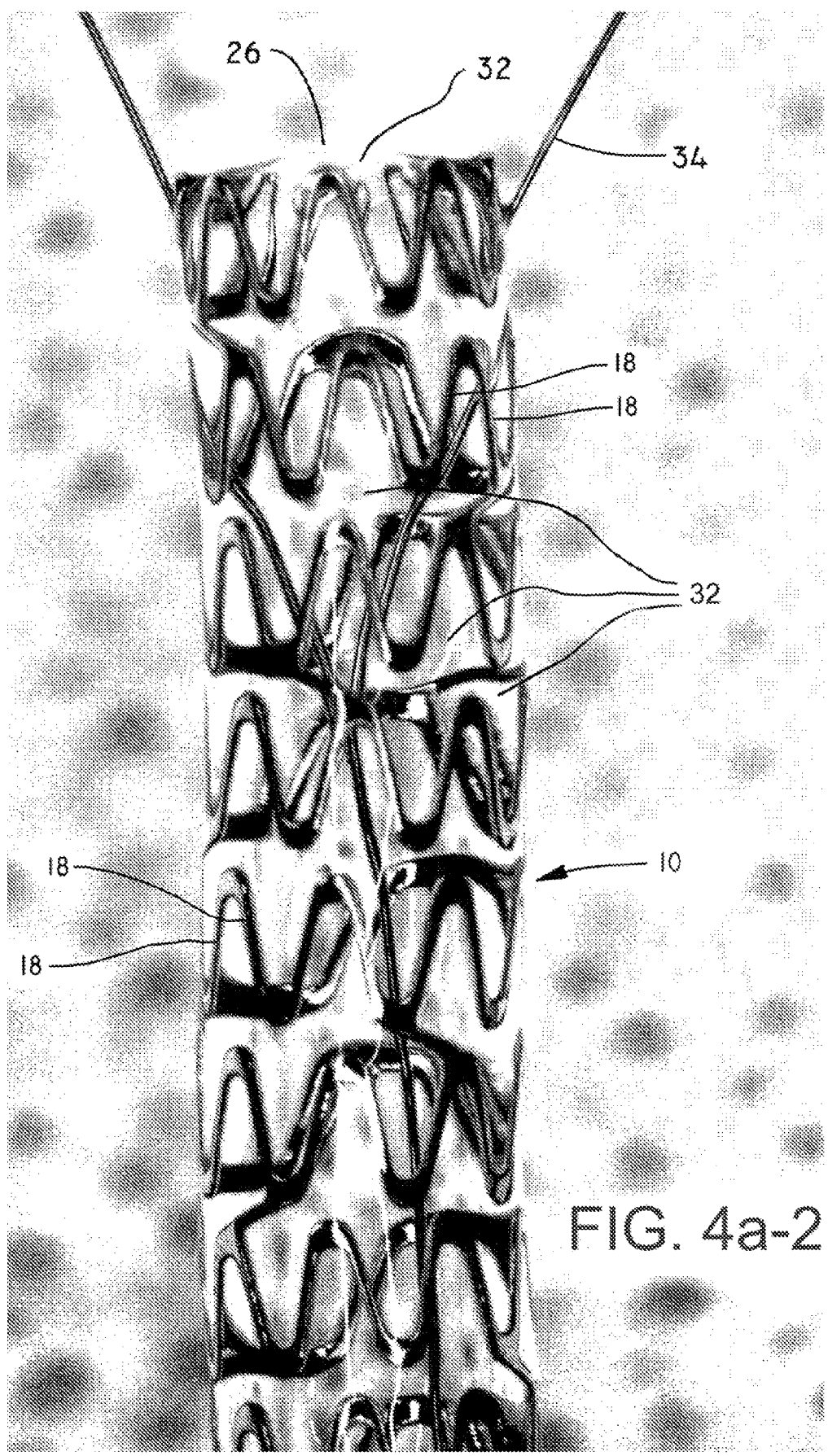
Figures 1, 4B:
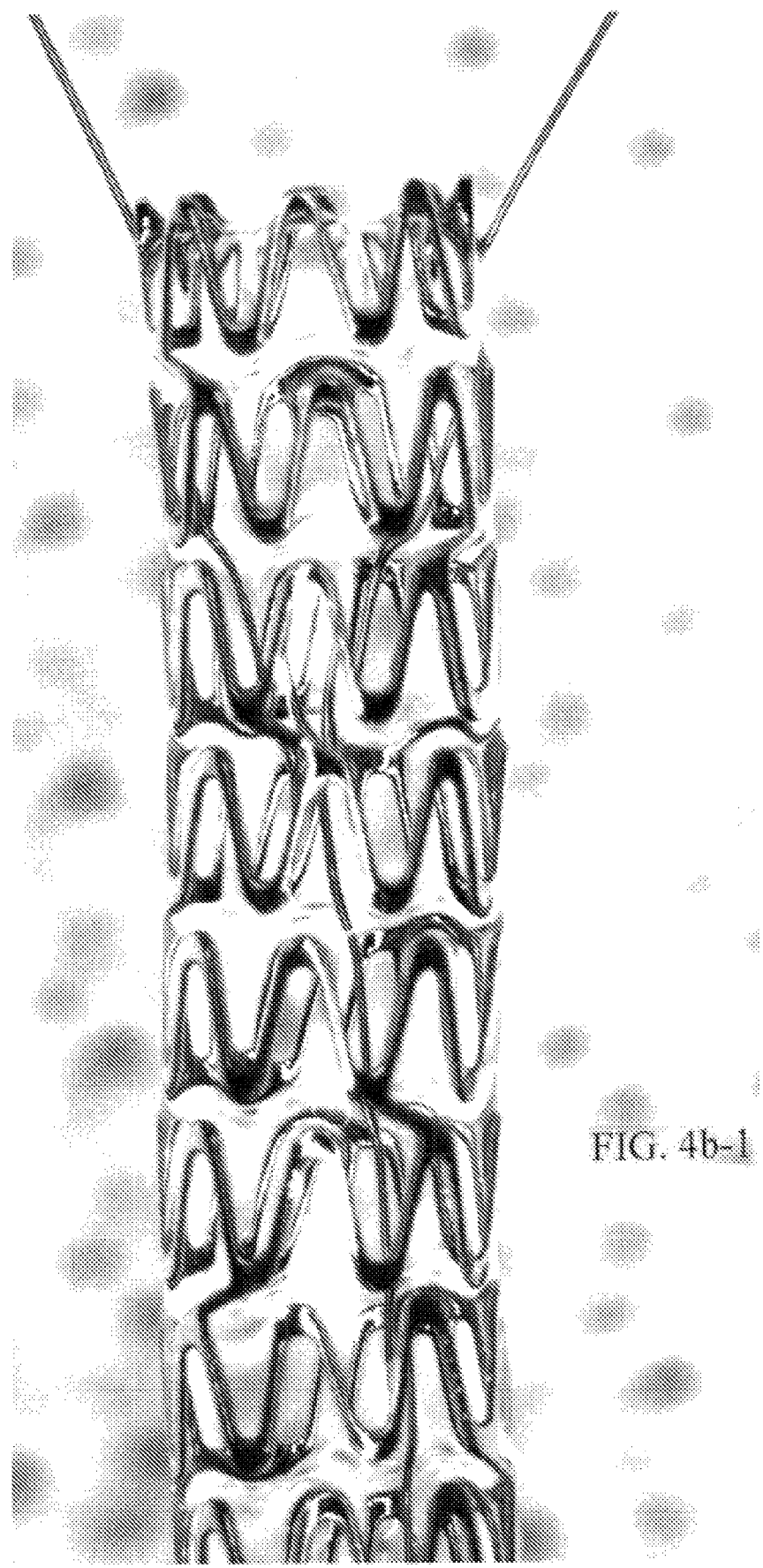
Figures 2, 4B:
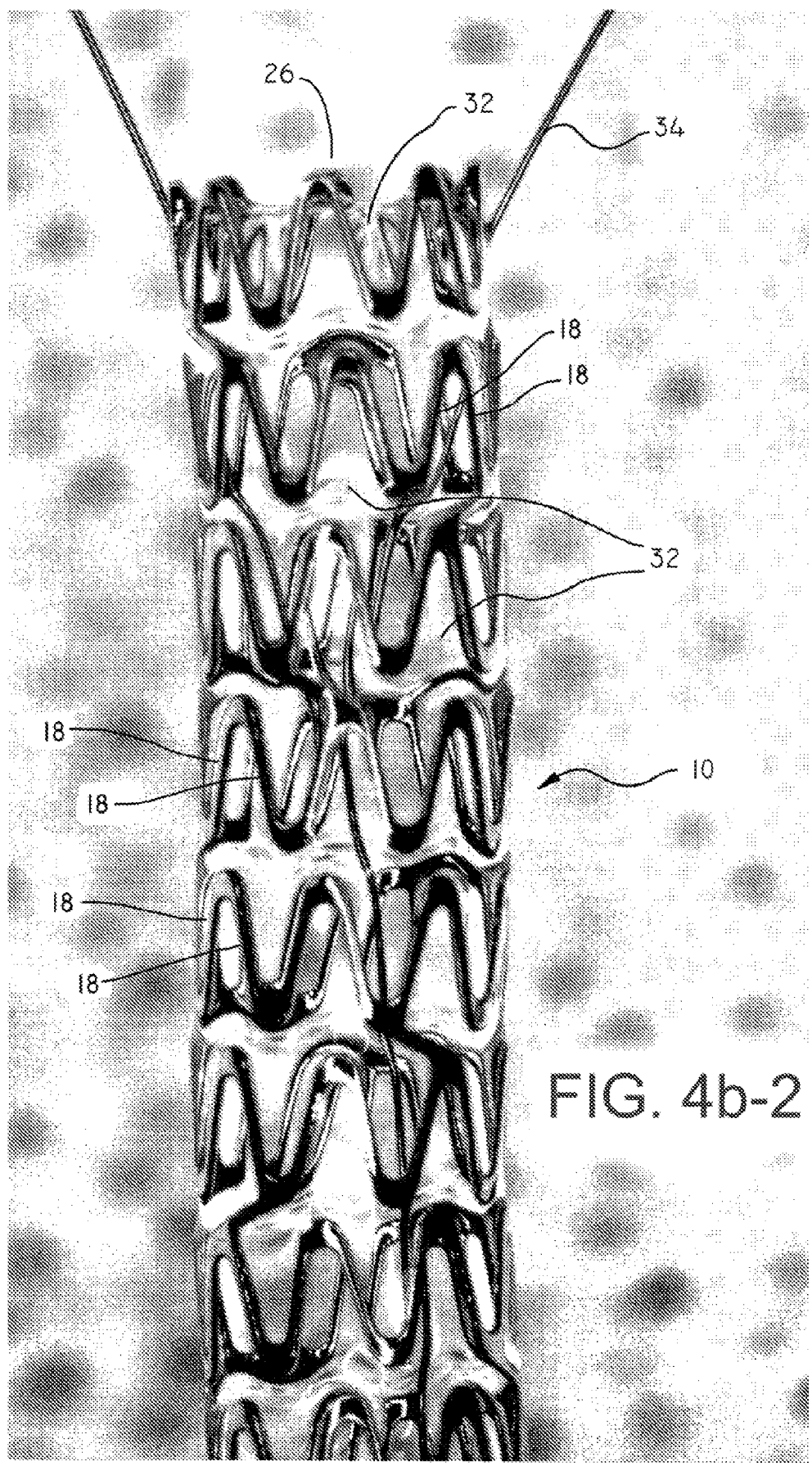

FIGS. 4a-1 and 4b-1 are optical digital views and FIGS. 4a-2 and 4b-2 are the simplified line art diagrams of the optical digital views illustrating a stent 10 having masking fluid 32, in this embodiment water, shown retained within the central lumen 26 of the stent 10. A wire 34 is shown threaded through the central lumen 26 which can be used for purposes of further treating the stent such as for spraying with a coating. In this embodiment, the inner diameter of the stent is about 2 mm. Stents employed in the coronary arteries may have inner diameters in the range of about 1 mm to about 4 mm. A fluid having a viscosity such as that of toluene, 0.59 cPs at 20° C., may be employed for stents having small inner diameters. Water, having a viscosity of about 1 cPs at 20° C., and xylene, having a viscosity of about 0.78 cPs at 20° C., may also be employed. The ability of the stent to retain the fluid also depends on surface tension as a function of volume to surface area ratio.

For stents with small inner diameters, the viscosity may be low, i.e., in the range of about 0.5 cPs to about 500 cPs, more suitably about 0.5 cPs to about 5 cPs at 20° C.

For larger diameters, more viscous fluids may be employed. For example, fluids having higher viscosities, such as those in the range of 2000-3000 cPs (viscosity similar to honey), can be employed for stents having larger diameter sizes.

In order to remove the stent 10 from the masking fluid 32 without disturbing the retention of the fluid within the central lumen, it may be desirable to first place the stent on some sort of fixture to facilitate submersion in the fluid and removal from the fluid without disturbing the fluid retained within the central lumen. The stent can be allowed to dry and can be coated on the same fixture as well.

Figure 5:
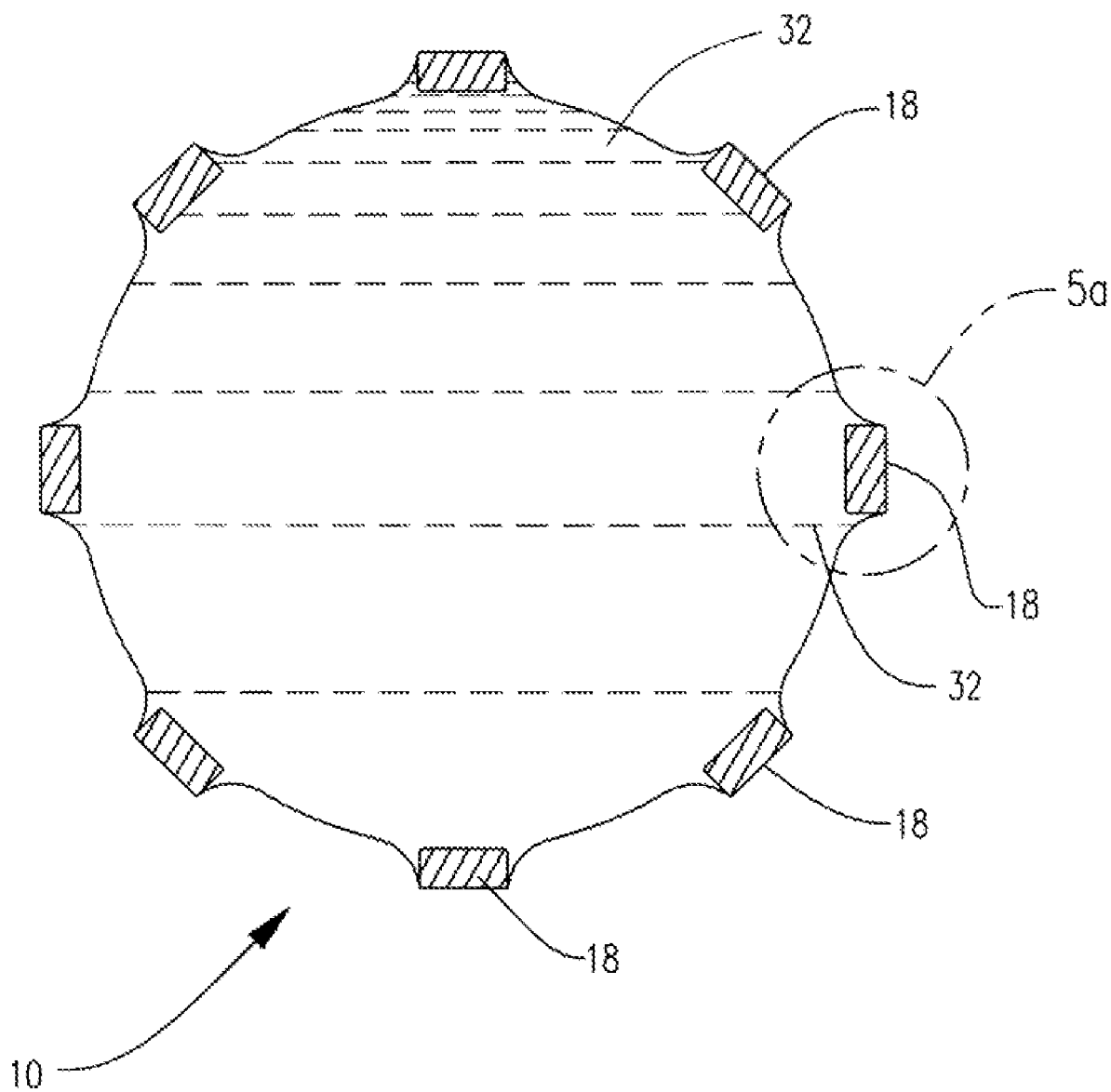
FIG. 5 is a radial cross-section of a stent similar to that shown in FIG. 1 taken at section 2-2 in FIG. 1 but with masking fluid filling the central lumen.
Figure 5A:
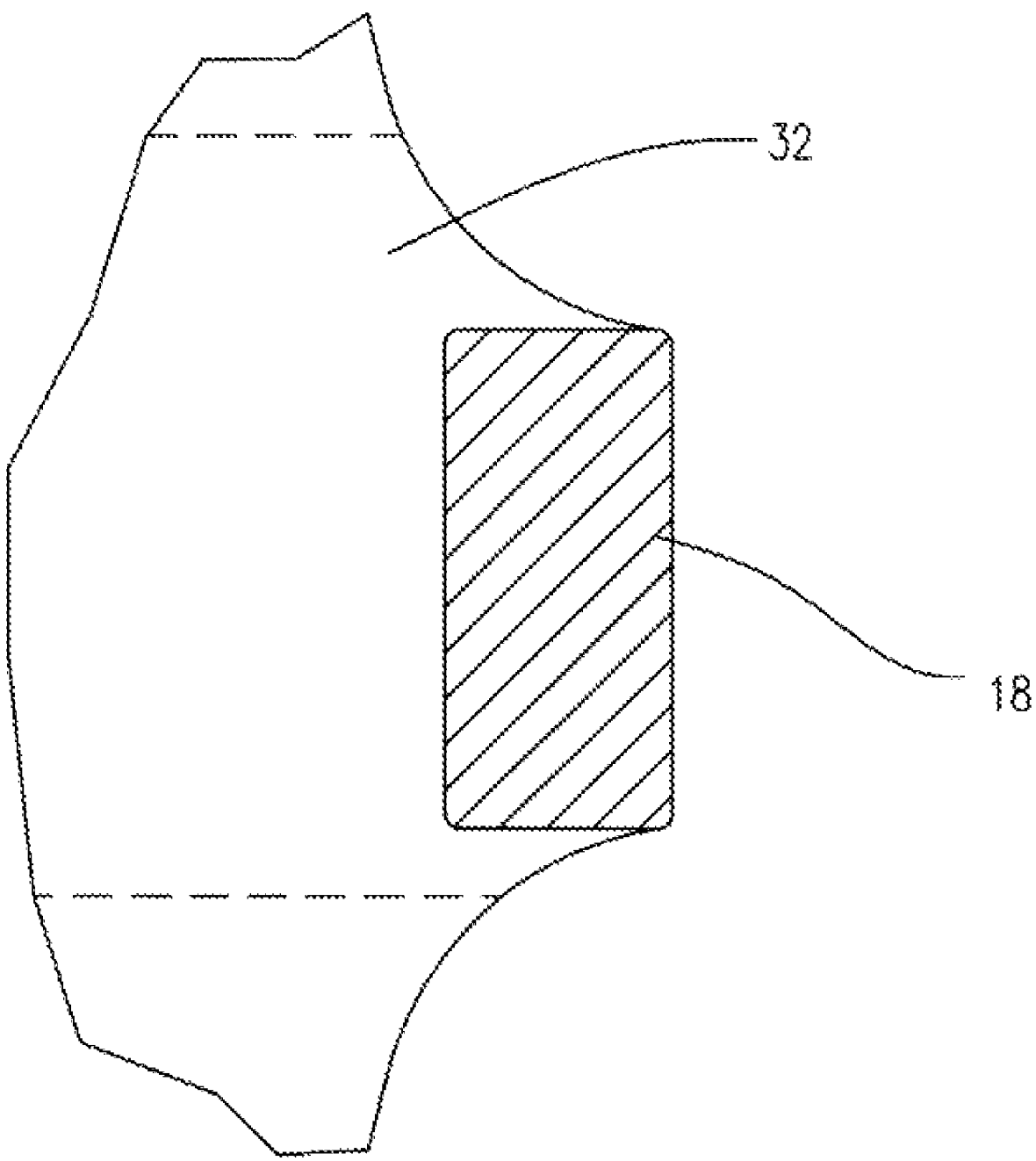
FIG. 5a is an enlarged view taken at section 5a in FIG. 5.

FIG. 5 is a radial cross-section of a stent similar to that shown in FIG. 1 taken at section 2-2 in FIG. 1 but showing masking fluid 32, in this embodiment water, filling the central lumen of stent 10. FIG. 5a is an enlarged view taken at section 5a in FIG. 5 showing the masking fluid 32 around an individual stent strut 18.

Figure 6:
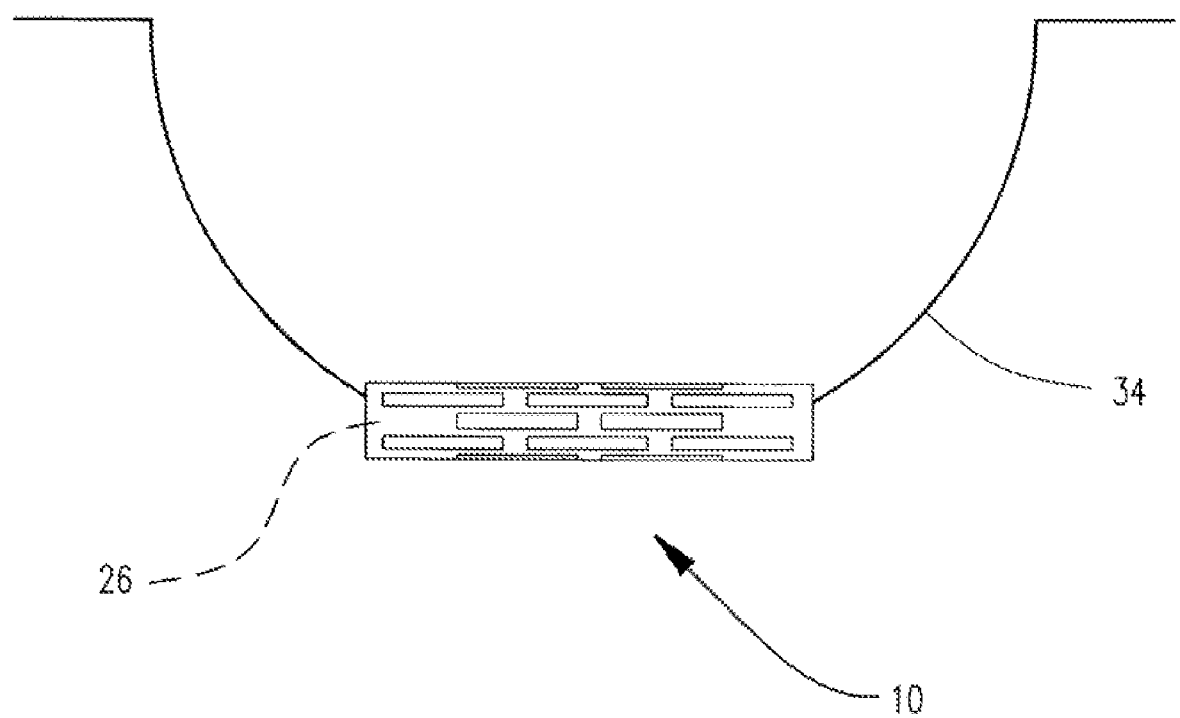
FIG. 6 is a sideview of stent on a wire for easy coating.

FIG. 6 is a side view of a stent 10 shown threaded through the central lumen 26 on a wire 34 to facilitate filling of the central lumen of stent 10.

Figure 7:
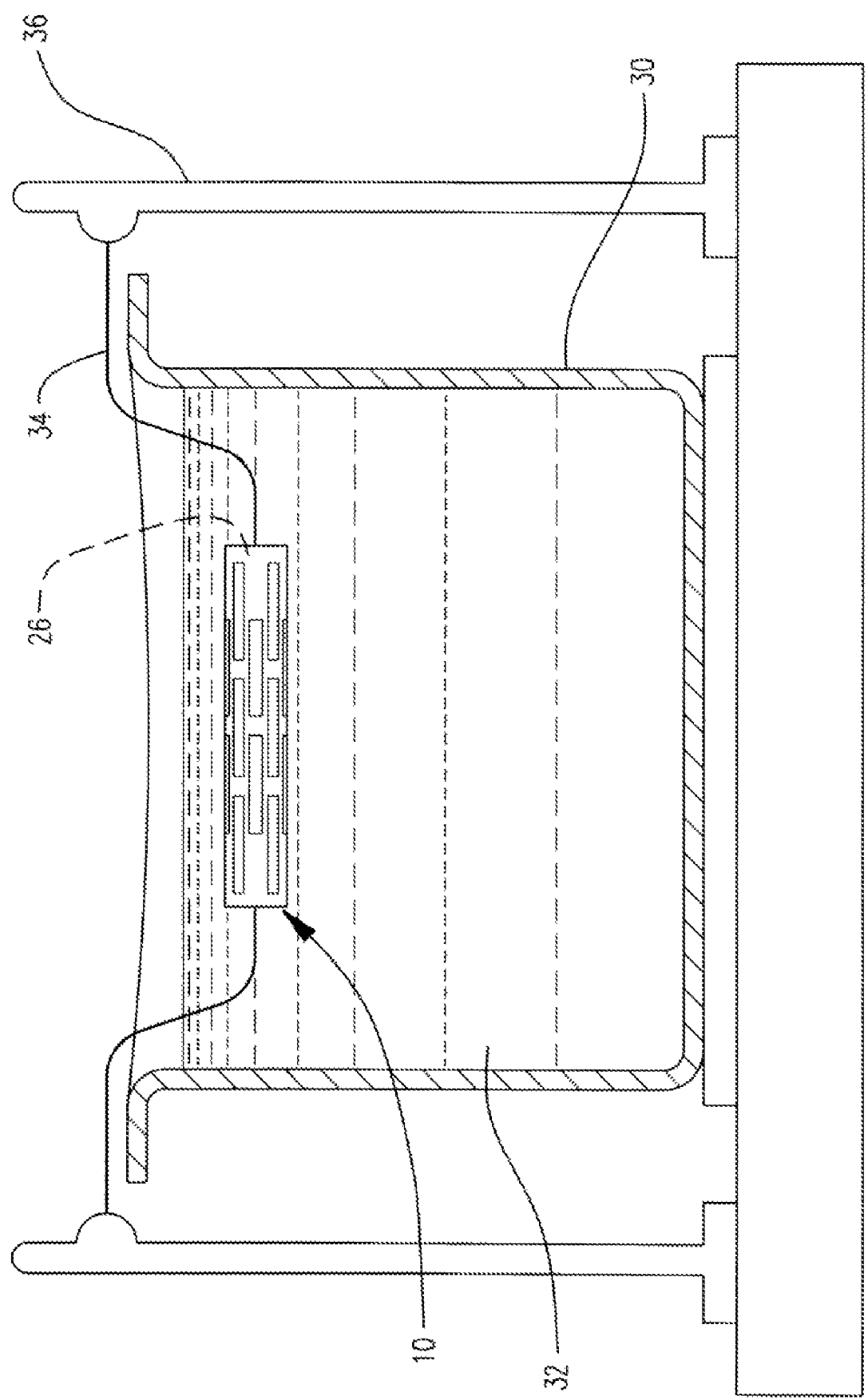
FIG. 7 is a side view of an apparatus to facilitate both filling of the stent with a masking fluid and coating of the stent showing the stent submersed in the masking fluid.
Figure 8:
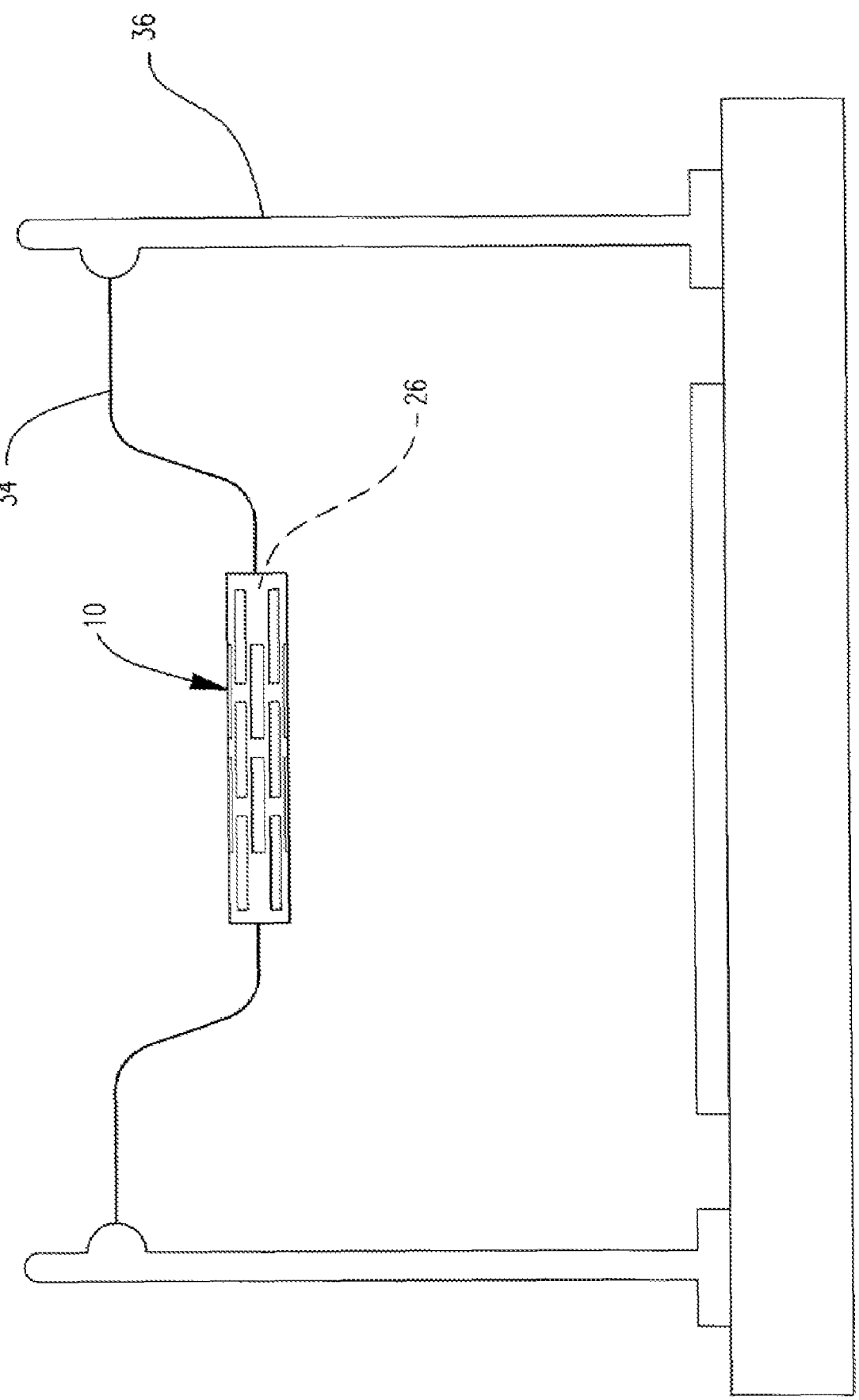
FIG. 8 is a side view of an apparatus to facilitate both filling the central lumen of the stent with a masking fluid and coating of the stent after removal of the vessel which holds the masking fluid.

Wire 34 could be further configured so as to be mounted on a support structure 36 as shown in FIG. 7. Stent 10 is shown submersed in a masking fluid 32 in vessel 30. The stent may be inserted end first in order to allow fluid to wick up into the central lumen. Such an apparatus allows for easy removal of the vessel 30 with masking fluid 32. FIG. 8 illustrates the apparatus after removal of vessel 30. Stent 10 can then be dried on support structure 36 and coated such as by spraying, brushing or roll coating, using the same support structure without further handling of the stent. The less handling required, the less likely that any damage will occur to the stent structure or to any coatings applied thereon during the manufacturing procedure. Furthermore, the coating method is selected so that it does not disrupt the masking fluid filling the central lumen. For example, if a spray method of application is employed, it is desirable to employ little or no gas pressure. Delivery gas pressure and velocity cannot be too high. If either the gas pressure or the velocity is too high, the masking fluid may be forced from the central lumen. For example, a gas pressure of about 30 psi or less is desirable, and suitably between about 5 psi and about 30 psi. However, this pressure range may be varied depending on other factors. For example, nozzle size and the distance of the stent from the nozzle will impact the velocity of the gas as it hits the stent surface. In any event, if the velocity of the masking fluid is too high, the force of the gas hitting the stent may result in masking fluid being forced from within the stent structure, and delivery gas forces should not exceed the capillary forces retaining the fluid within the stent structure.

Figure 9:
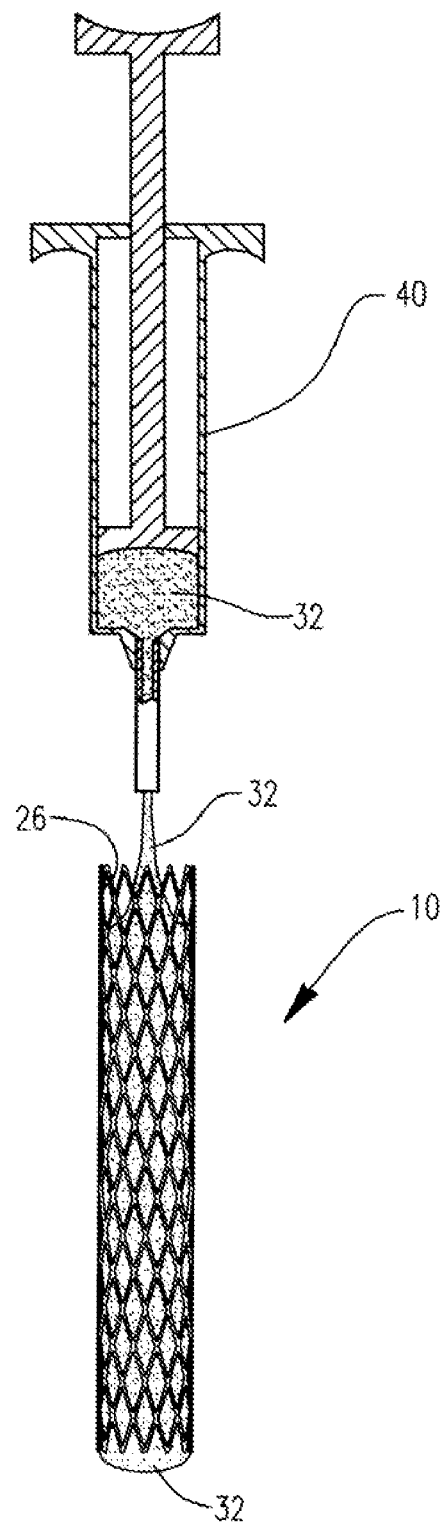
FIG. 9 is a side view illustrating an alternative method of filling the central lumen of the stent.

Other methods of filling the central lumen of the stent may be employed. For example, as shown in FIG. 9, a syringe 40 containing masking fluid 32 may be employed to fill the central lumen 26 of stent 10.

While for some coating methods it may be advantageous to employ such a support structure, for other methods such as roll coating, such a support structure may not be as advantageously employed.

An alternative method suitable for application of a coating is a drop-on-demand coating method. Using drop-on-demand applications, there are conditions where desired drop size and/or stability are not possible with some coatings and orifice combinations. By addition of a masking fluid to the stent lumen, the stent may be selectively coated using the precision of drop-on-demand. The term "drop-on-demand" refers to any active or passive release of a predetermined drop or number of drops equivalent to a desired quantity of coating material. See U.S. Pat. Nos. 7,048,962, 6,916,379 and 6,645,547, each of which is incorporated by reference herein in its entirety. See also, WO 2005/025455, the entire content of which is incorporated by reference herein. An example of this technology is the piezo drop-on-demand technology such as that manufactured by Ink Jet Technology, Inc. of San Jose, Calif. which provides applicators for a wide variety of coating applications.

Any suitable coating method can be employed providing it does not disrupt the masking fluid filling the central lumen.

The method according to the invention may be used to selectively coat the outer surface of the stent with any desirable coating composition.

Suitable coating compositions may include, for example, compounds to improve stent visibility, biocompatible polymers, lubricious polymers, therapeutic agents, etc.

Examples of suitable polymers which may be employed in the coating compositions include biodegradable homopolymers and copolymers including, but not limited to, polylactic acid, polyhydroxyvalerate-hydroxybutyrate, polycaprolactone, polyglycolic acid, copolymers of lactic acid and glycolic acid, etc. As used herein, the term copolymer shall refer to those polymers formed with two or more different monomers including terpolymers and so forth.

Other examples of suitable polymers which may be employed in the coating composition include styrenic block copolymers including, but not limited to, styrene-butadiene-styrene (SBS), styrene-ethylene/butylene-styrene (SEBS), styrene-isoprene-styrene (SIS), styrene-isobutylene-styrene (SIBS), etc.

Other polymers which may be employed include, but are not limited to, fluoropolymers such as polytetrafluoroethylene and fluorinated ethylene-propylene, polyolefins including polyethylene and polypropylene as well as copolymers of ethylene and propylene, polyamides (i.e. nylons), polyimides, polyethers, polyesters and copolyesters, polyurethanes, silicone, polycarbonates, polysulfones, block copolymer elastomers such as poly(ether-block-amide), polyether-ester block copolymers and polyester-ester block copolymers, etc.

Examples of suitable lubricious polymers include, but are not limited to, polyalkylene glycols, alkoxy polyalkylene glycols, polyalkylene oxides, polyvinyl pyrrolidone, polyvinyl alcohol, polyacrylamides, copolymers of maleic anhydride, a polyethylene oxide hydrogel polymer captured in an interpenetrating crosslinked acrylic polymer network, polycarboxylic acids, (meth)acrylic acid homopolymers and copolymers, copolymers of acrylic acid, methacrylic acid, maleic acid, fumaric acid or other polymerizable ethylenically unsaturated acids, etc. Lubricious polymers are disclosed in commonly assigned U.S. Pat. Nos. 5,509,899, 5,693,034, 6,221,646, the entire contents of which are incorporated by reference herein in their entirety.

Examples of therapeutic agents are listed in commonly assigned copending U.S. Patent Publication No. 2004/0215169 and in U.S. Pat. No. 6,855,770, each of which is incorporated by reference herein in its entirety.

The above lists are intended for illustrative purposes only, and not as a limitation on the scope of the present invention.

Once the outer surface has been coated as desired, the masking fluid may be removed from the central lumen using any suitable method such as by flushing with an appropriate fluid, wiping, wicking, or evaporation of the masking fluid.

The inventive stents may find use in coronary arteries, renal arteries, peripheral arteries including illiac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770, each of which is incorporated by reference herein in its entirety. More generally, any known graft material may be used including synthetic polymers such as polyethylene, polypropylene, polyurethane, polyglycolic acid, polyesters, polyamides, their mixtures, blends, copolymers, mixtures, blends and copolymers.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The invention claimed is:

1. A method of selectively coating a medical device having a tubular wall, the tubular wall having an inner surface and an outer surface, the inner surface of the tubular wall defining a central lumen, the medical device further having openings extending from the outer surface of the tubular wall to the inner surface of the tubular wall, the method comprising the steps of:
   filling the central lumen with a masking fluid wherein said masking fluid is retained in said central lumen and said outer surface is free of said masking fluid; and
   applying a coating composition to at least a portion of the outer surface of the medical device.

2. The method of claim 1 wherein said coating composition is applied to the entire outer surface.

3. The method of claim 1 wherein said central lumen of said medical device is filled with said masking fluid by fully submersing said medical device in said masking fluid.

4. The method of claim 1 wherein said outer surface of said tubular wall is dried prior to applying said coating composition.

5. The method of claim 1 wherein said coating composition comprises at least one biocompatible material.

6. The method of claim 1 wherein said coating composition comprises at least one therapeutic agent.

7. The method of 1 wherein said coating composition is applied from a solvent or a cosolvent blend.

8. The method of claim 1 wherein said coating composition is applied by spraying said coating composition on said outer surface of said medical device.

9. The method of claim 8 wherein said coating composition is applied by spraying said coating composition using a carrying gas pressure that adequately provides said coating composition to said outer surface of said medical device without displacement of said masking liquid from said central lumen of said medical device.

10. The method of claim 8 wherein said coating composition is applied by spraying said coating composition using pressures of about 5 psi to about 30 psi.

11. The method of claim 1 wherein said coating composition is applied to the outer surface of said medical device by brushing said coating composition on said device.

12. The method of claim 1 further comprising the step of removing said masking fluid from said central lumen.

13. The method of claim 12 wherein said step of removing said masking fluid from said central lumen is accomplished by wiping, wicking or evaporating said masking fluid from said central lumen.

14. The method of claim 1 wherein said masking fluid is a polar or a non-polar solvent.

15. The method of claim 1 wherein said masking fluid is water.

16. The method of claim 1 wherein said masking fluid is a hydrocarbon solvent.

17. The method of claim 16 wherein said masking fluid is xylene or toluene.

18. The method of claim 1 wherein said medical device has at least one unexpanded state and at least one expanded state, and the inner surface of said tubular wall of the medical device defines an inner diameter, the inner diameter of the medical device in the at least one unexpanded state being about 1 mm to about 4 mm.

19. The method of claim 1 wherein said medical device is a stent.

20. The method of claim 18 wherein said masking fluid has a viscosity of about 0.5 cPs to about 500 cPs at 20° C.

21. The method of claim 18 wherein said masking fluid has a viscosity of about 0.5 cPs to about 5 cPs at 20° C.

22. A method for selectively coating an outer surface of a tubular member, the tubular member comprising an inner surface which defines a central lumen, the tubular member further comprising openings which extend through the outer surface and the inner surface of the tubular member, the method comprising filling the central lumen with a masking fluid which is retained in the central lumen by surface tension, wherein the outer surface is free of masking fluid and applying a coating composition to at least a portion of the outer surface of the medical device.

* * * * *